(12) United States Patent
Nordin et al.

(10) Patent No.: US 10,342,644 B2
(45) Date of Patent: Jul. 9, 2019

(54) DENTAL IMPLANT

(76) Inventors: Peter Nordin, Chernex (CH); Harald Nordin, Chernex (CH)

( * ) Notice: Subject to any disclaimer, the term of this patent is extended or adjusted under 35 U.S.C. 154(b) by 0 days.

(21) Appl. No.: 13/358,785

(22) Filed: Jan. 26, 2012

(65) Prior Publication Data

US 2012/0288824 A1    Nov. 15, 2012

(30) Foreign Application Priority Data

May 10, 2011    (EP) ..................... 11165560

(51) Int. Cl.
*A61C 8/00*    (2006.01)
(52) U.S. Cl.
CPC ............ *A61C 8/0086* (2013.01); *A61C 8/005* (2013.01); *A61C 8/0069* (2013.01); *A61C 8/0063* (2013.01)
(58) Field of Classification Search
CPC ....... A61C 8/005; A61C 8/006; A61C 8/0018; A61C 8/0054; A61C 8/0069
USPC .......................................... 433/172–177, 225
See application file for complete search history.

(56) References Cited

U.S. PATENT DOCUMENTS

| | | | | |
|---|---|---|---|---|
| 3,971,134 A | * | 7/1976 | Bokros | 433/201.1 |
| 4,195,409 A | * | 4/1980 | Child | 433/175 |
| 4,252,525 A | * | 2/1981 | Child | 433/173 |
| 4,609,354 A | * | 9/1986 | Koch | A61C 8/0018 433/173 |
| 5,026,280 A | * | 6/1991 | Duerr et al. | 433/175 |
| 5,328,372 A | * | 7/1994 | Reynaud et al. | 433/220 |
| 5,360,482 A | | 11/1994 | Belvedere | 118/404 |
| 5,453,007 A | * | 9/1995 | Wagher | 433/177 |
| 5,509,804 A | * | 4/1996 | Arzt | 433/169 |
| 5,584,693 A | | 12/1996 | Nishihara | 433/169 |
| 5,797,748 A | * | 8/1998 | Reynaud et al. | 433/224 |
| 5,816,816 A | * | 10/1998 | Scharf | 433/220 |
| 5,853,653 A | * | 12/1998 | Donato et al. | 264/625 |
| 5,861,445 A | | 1/1999 | Xu et al. | 523/116 |
| 5,890,904 A | * | 4/1999 | Reynaud et al. | 433/220 |
| 5,919,044 A | * | 7/1999 | Sicurelli et al. | 433/220 |
| 5,921,778 A | | 7/1999 | Karmaker et al. | 433/215 |
| 5,954,505 A | * | 9/1999 | Ford | 433/177 |

(Continued)

FOREIGN PATENT DOCUMENTS

DE    20 2010 008 938 U1    2/2011
EP       1 147 748 A2    10/2001

(Continued)

OTHER PUBLICATIONS

European Search Report dated Oct. 19, 2011 issued in connection with corresponding European patent application No. EP 11 16 5560.

(Continued)

*Primary Examiner* — Cris L. Rodriguez
*Assistant Examiner* — Matthew P Saunders
(74) *Attorney, Agent, or Firm* — Ostrolenk Faber LLP (57) ABSTRACT

The invention relates to a dental implant configured to be anchored in a jawbone for supporting a dental prosthesis. In order to allow an adjustment of the tooth restoration structure to properties of a natural tooth the dental implant includes a jacket member which includes at least in part an osseo-integratable material and enclosing a cavity in an apical direction, and a filling member of fiber reinforced material and being shaped so as to substantially fill out the cavity.

39 Claims, 5 Drawing Sheets

(56) References Cited

U.S. PATENT DOCUMENTS

| | | | |
|---|---|---|---|
| 6,030,220 A | 2/2000 | Karmaker et al. | 433/215 |
| 6,083,004 A | 7/2000 | Misch et al. | 433/173 |
| 6,193,516 B1* | 2/2001 | Story | A61C 8/0086 |
| | | | 433/173 |
| 6,267,597 B1* | 7/2001 | Kim | 433/224 |
| 6,287,122 B1* | 9/2001 | Seeram et al. | 433/220 |
| 6,371,763 B1* | 4/2002 | Sicurelli et al. | 433/220 |
| 6,381,989 B1 | 5/2002 | Karmaker et al. | 65/384 |
| 6,402,519 B1* | 6/2002 | Nordin | 433/220 |
| 7,235,290 B2 | 6/2007 | Vallittu et al. | 428/296.7 |
| 7,335,250 B2* | 2/2008 | Burtscher et al. | 106/35 |
| 7,673,550 B2 | 3/2010 | Karmaker et al. | 87/1 |
| 7,682,152 B2* | 3/2010 | Ford et al. | 433/174 |
| 7,850,452 B2* | 12/2010 | Suttin et al. | 433/174 |
| 7,887,327 B2 | 2/2011 | Marotta | 433/213 |
| 7,997,901 B2* | 8/2011 | Karmaker | 433/224 |
| 2002/0025506 A1 | 2/2002 | Hagenbuch et al. | 433/201.1 |
| 2003/0057590 A1* | 3/2003 | Loher | A61B 17/866 |
| | | | 264/157 |
| 2004/0053194 A1 | 3/2004 | Carroll | 433/172 |
| 2004/0234925 A1* | 11/2004 | Benhamou | 433/173 |
| 2005/0266380 A1* | 12/2005 | Soler et al. | 433/173 |
| 2005/0266382 A1* | 12/2005 | Soler et al. | 433/173 |
| 2006/0208393 A1 | 9/2006 | Karmaker et al. | 264/230 |
| 2007/0141532 A1* | 6/2007 | Ford et al. | 433/173 |
| 2007/0141535 A1* | 6/2007 | Baldissara | 433/220 |
| 2008/0020343 A1 | 1/2008 | Mount | 433/172 |
| 2008/0124682 A1* | 5/2008 | Nordin | A61C 3/02 |
| | | | 433/220 |
| 2008/0261176 A1 | 10/2008 | Hurson | 433/174 |
| 2009/0061385 A1* | 3/2009 | Bahcall et al. | 433/173 |
| 2009/0061389 A1 | 3/2009 | Lomicka et al. | 433/201.1 |
| 2009/0092950 A1* | 4/2009 | Machado | 433/225 |
| 2009/0123888 A1* | 5/2009 | Rosenberg | 433/173 |
| 2009/0123891 A1* | 5/2009 | Rosenberg | 433/174 |
| 2009/0176192 A1 | 7/2009 | Vallittu et al. | 433/215 |
| 2009/0258965 A1 | 10/2009 | Lassila et al. | 523/116 |
| 2010/0119994 A1* | 5/2010 | Feith | A61C 8/005 |
| | | | 433/173 |
| 2010/0151420 A1 | 6/2010 | Ranck | 433/173 |
| 2010/0209877 A1 | 8/2010 | Hogan et al. | 433/214 |
| 2010/0304334 A1* | 12/2010 | Layton | 433/173 |
| 2011/0033828 A1* | 2/2011 | Nordin et al. | 433/221 |
| 2011/0250568 A1 | 10/2011 | Machado | 433/225 |
| 2012/0107773 A1* | 5/2012 | Lu et al. | 433/173 |
| 2012/0288825 A1 | 11/2012 | Nordin et al. | 433/173 |
| 2014/0162215 A1 | 6/2014 | Feith | 433/174 |

FOREIGN PATENT DOCUMENTS

| | | | | |
|---|---|---|---|---|
| EP | 1 319 375 A1 | 6/2003 | | |
| EP | 1319375 A1 * | 6/2003 | | A61C 13/30 |

OTHER PUBLICATIONS

European Search Report dated Oct. 19, 2011 in related European Patent Application No. EP 11165565.0.

"Introduction to composite materials," F.C. Campbell—Structural composite materials—2010 ASM International.

* cited by examiner

DENTAL IMPLANT

FIELD OF THE INVENTION

The invention relates to a dental implant configured to be anchored in a jawbone for supporting a dental prosthesis.

BACKGROUND OF THE INVENTION

Prosthodontic restorations replacing a natural tooth in a patient's dentition are commonly fixed on a dental implant that is surgically implanted into the patient's jawbone. Typically, since the early work of Per-Ingvar Brånemark of Sweden in 1952, such an implant consists of a titanium screw which resembles a tooth root and comprises a roughened or smooth surface. The majority of dental implants are made out of pure titanium, which is commercially available in four grades depending upon the amount of contained carbon and iron.

An abutment is usually anchored at the coronal end of the dental implant. A dental prosthesis, such as a crown, a fixed bridge retainer or a removable denture, can be attached on the abutment serving as an interface between the dental prosthesis and the dental implant. The abutment is typically held in place with a screw. Abutments can be custom-made in a dental laboratory or purchased as a prefabricated part from a dental implant supplier.

Current implants are typically made of titanium, stainless steel or ceramics. The biocompatibility of these materials has been widely documented over the years, especially in the case of titanium and ceramics. Despite this benefit, all these materials have the disadvantage of being too stiff and brittle as compared to the dentine and cementum of a natural tooth they are supposed to replace and mimic. In consequence, the masticatory stresses exerted on the artificial tooth structure cannot be adequately absorbed. This leads to a number of undesirable side effects including an unnatural feeling of pressure while chewing, increased bruxism, and an increased risk of breakage of the artificial tooth structure. Another disadvantage lies in the different refractive index of these materials as compared to a natural tooth, resulting in an unnatural and unaesthetic appearance of the replacement structure. Moreover, these materials are difficult to rework, in particular to cut or grind or trim. In consequence, they are usually fabricated in specific standardized shapes which complicates an individual adaption to the shape of crown or bridge restorations.

OBJECTS AND SUMMARY OF THE INVENTION

It is an object of the present invention to avoid at least one of the above mentioned disadvantages and to provide an improved dental implant which allows an adjustment of the tooth restoration structure to properties of a natural tooth.

The dental implant according to the invention comprises a jacket member consisting at least in part of an osseointegratable material and enclosing a cavity in an apical direction, and a filling member consisting of fiber reinforced material and being shaped so as to substantially fill out the cavity of the jacket member. In this way, the two advantages of an unproblematic osseointegration of the implant and an assimilation to the mechanical properties, in particular to the modulus of elasticity, of a natural tooth can be effectively combined.

In general terms, it can be expected that the improvement of the mechanical properties of the implant increases with the amount of cavity volume that is filled with the filling member. Thus, an improvement may already be achieved by a cavity that constitutes a volume of 20% or less of the jacket member. Preferably, the cavity constitutes at least one third, more preferred at least one half, and most preferred at least two third of the volume of the jacket member. According to a preferred implementation, the upper limit of the cavity volume is determined based on the minimum thickness of the walls of the jacket member that are needed to ensure osseointegration of the implant. Preferably, the wall thickness of the jacket member is at least 0.2 mm, more preferred at least 0.5 mm, to ensure a sufficient rigidity for mounting of the implant.

In order to allow an advantageous mounting of the implant, the jacket member preferably comprises a coronal opening and the filling member is insertable into said jacket member through the coronal opening. In particular, the following procedure of mounting of the implant may be applied: First, the jacket member is anchored in the jawbone of a patient in a surgical operation. Optionally, a healing cap is then temporarily inserted in the cavity through the coronal opening. After healing, the healing cap is removed and the filling member is inserted into the cavity and rigidly fixated therein. Various fixation methods are conceivable, such as cementing, screwing, fixing, clipping, or a combination thereof.

The coronal opening preferably extends over at least 20% of the coronal side of said jacket member in order to allow the insertion of a filling member that allows an observable improvement of the mechanical properties of the implant. More preferred, the coronal opening extends over at least 50%, more preferred over at least 70%, and most preferred over at least 90% of the coronal side of said jacket member for allowing an uncomplicated insertion of a filling member providing a notable improvement of the mechanical properties. Preferably, the jacket member has a shape in accordance with the tooth anatomy. In particular, a cylindrical, conical, pyramidal or hyperboloidal shape is conceivable with sizes adapted to the anatomical configuration to be replaced.

According to a preferred configuration, the jacket member comprises an anchoring member consisting of the osseointegratable material and a sleeve member that is insertable into the anchoring member, such that the cavity is enclosed by the sleeve member. Thus, the sleeve member defining the inner cavity for the filling member is insertable, and if required also removable, from the anchoring member that is anchored and osseointegrated into the jawbone. In this way, the sleeve member can serve as a container for the filling member which facilitates the insertion and/or removal of the filling member into and/or from the portion of the implant that is anchored in the jawbone. Such a removable container may be particularly advantageous in the case of a fracture or crumbling of the fibrous material constituting the filling member. Preferably, the sleeve member consists of the same or similar material as the anchoring member. Suitable materials for the anchoring member and/or the sleeve member are for instance titanium, stainless steel or ceramics. The sleeve member can be attached to the anchoring member by cementing, screwing, fixing, clipping, or a combination thereof.

According to an alternative preferred configuration, the jacket member may only consist of an anchoring member consisting of the osseo-integratable material, such that the cavity is enclosed by the anchoring member. In this case, the filling member may be advantageously removable from the cavity, e.g. in case of a fracture of the filling member, by means of drilling. In order to allow such a drilling, the invention suggests providing a reamer that is preferably adjusted to the shape of the cavity of the jacket member. The fibrous structure of the filling member according to the invention permits an unproblematic removal by the drilling with the reamer.

In order to improve the osseointegration properties of the implant, the jacket member comprises walls with an increasing thickness towards the apical end. Preferably, the thickness is increasing continuously. According to an alternative embodiment, the jacket member preferably comprises walls with a substantially constant thickness, such that the filling member can be equally distributed over the volume of the implant. Preferably, the wall thickness of the jacket member is chosen in such a way that the jacket member is stable enough to be implanted and anchored into the jawbone and provides an unproblematic osseointegration of the implant. According to a preferred configuration, the jacket member comprises walls with a thickness of at most 10 mm, more preferred at most 3 mm, and most preferred at most 1 mm for enclosing said cavity.

According to a first preferred embodiment, the filling member has a coronal height that substantially corresponds to the coronal height of the cavity. In this case, the coronal surface of the filling member is preferably adapted to allow a rigid connection with an abutment, serving as an interface between the filling member and a dental implant. Preferably, the abutment comprises a body portion for supporting the dental prosthesis and a contact surface apical to said body portion for contacting the filling member. Preferably, the abutment consists of the same material as the filling member. According to a second preferred embodiment, the filling member has a coronal height that exceeds the coronal height of the cavity. In this case, the exceeding portion at the coronal end of the filling member constitutes an abutment for a dental prosthesis.

Various fiber structures are conceivable to constitute the material of the filling member, in particular ordered fibers or randomly distributed fibers. In particular, small particle fibers, chopped fibers, long fibers or a composition thereof are conceivable. According to a preferred configuration, the filling member is composed of a resin that is reinforced with fibers substantially extending over its total length. The proposed material composition of the filling member allows the properties of natural dentine and/or cementum to be mimicked in a number of ways, in particular with respect to the modulus of elasticity and/or the refractive index. Moreover, the shape and size of the filling member can be easily reworked, even after its application in the jawbone, since the proposed material can be trimmed or cut similar to natural dentine.

Despite its smooth workability, a high flexural strength of the filling member can be achieved, in particular in the range of 1500 MPa or higher, due to the continuos longitudinal arrangement of the fibers. Thus, the filling member can be highly resistant against fracture, bending or rupture and can provide a long durability.

Generally, a number of different materials of the fiber and/or resin constituents of the filling member are conceivable. For instance, the material of the resin may be selected from methyl metacrylate (MMA), urethane dimethacrylate (UDMA), bisgma, epoxy, peek optima, polyester, polyvinyl ester or a mixture thereof. The material of the fibers may be selected from glass, quartz, carbon, aramide, kevlar or a mixture thereof. Moreover, a wide range of different compositions of the fiber content with respect to the resin content of the filling member is conceivable. Advantageously, the individual properties of these materials and of their relative composition can be exploited to adapt the filling member with respect to the specific requirements of the respective dental structure to be replaced.

In order to reduce the risk of breakage of the filling member, its modulus of elasticity is at least 10 GPa and at most 50 GPa. In this way, the elastic properties of natural dentine and/or cementum can be imitated.

Preferably, the longitudinal extension of the fibers within the resin is exploited in such a way, that an anisotropic modulus of elasticity is achieved within the filling member. Thus, the filling member preferably exhibits a modulus of elasticity that varies in dependence on the direction of a force applied to the filling member with respect to the orientation of a longitudinal axis extending in the apical direction of the filling member. In this way, the inherent properties of a natural two-layer system, such as in between enamel and dentine or dentine and cementum can be further simulated.

More precisely, an anisotropic behavior of the modulus of elasticity of natural enamel and dentine has been reported in various scientific studies. Such an anisotropic behavior of at least one layer of a multilayered biological system is believed to contribute to a protection against breakage or rupture of the system. Advantageously, the filling member according to the invention can be used to mimic the anistropic elastic modulus of one layer of such a natural system.

Preferably, the modulus of elasticity is lower for a force applied perpendicularly to the longitudinal axis of the filling member than for a force applied parallel to its longitudinal axis. In this way, a homogenous and therefore predictable behavior can be achieved over the whole length of the filling member. Preferably, the fiber content is chosen in such a way, that a variation of the elastic modulus of at least 10 GPa, more preferred at least 30 GPa is achieved. Furthermore, the fiber content is preferably chosen in such a way, that a variation of the elastic modulus of at most 100 GPa, more preferred at most 40 GPa is achieved. More specifically, the modulus of elasticity preferably varies between a value of at most 20 GPa for a force applied perpendicularly to said longitudinal axis and a value of at least 30 GPa for a force applied parallel to said longitudinal axis.

Various possibilities of the arrangement of the fibers within the resin are conceivable. According to a first preferred configuration, at least part of said fibers are substantially uniformly directed parallel to a longitudinal axis of said filling member. According to a second preferred configuration, at least part of said fibers are arranged in the manner of a braided netting in a biaxial or multiaxial orientation. Such an arrangement of the fibers can further contribute to improve the flexural strength of the filling member. In particular, an arrangement of the fibers can be applied as described in patent application No. EP 1 078 608 A1, which is hereby incorporated by reference.

A highly preferred material composition of the filling member comprises a resin that is derived from at least one methacrylate monomer, in particular methyl methacrylate (MMA) and/or urethane dimethacrylate (UDMA). Besides a high biocompatibility, an excellent bonding interaction at the surface of the filling member can be expected from this material selection due to a chemical composition that resembles currently used composite resin cements that are used for fixing prosthetic devices in dentistry.

To provide a filling member that optically resembles the properties of natural dentine, in particular to render the implant aesthetically more pleasing, the fibers are preferably constituted by glass fibers. For instance, E glass, S glass and/or AR Glass fibers are conceivable for that purpose. To further allow the filling member to simulate the optical properties of natural dentine, mineral particles are preferably embedded in said resin, wherein the content by volume of said mineral particles is provided such that the index of refraction of said filling member is between 1.3 and 1.8, more preferably between 1.4 and 1.6. An index of refraction between 1.50 and 1.55 is most preferred and is achieved by an appropriate composition of said resin, fibers and mineral particles in order to closely imitate the appearance of natural dentine.

In use, a basic prerequisite of the implant is its radiopacity to allow a dentist to monitor the artificial tooth structure by X-ray analysis. In order to provide this property of the filling member, X-ray absorbing particles are preferably embedded in said resin, said X-ray absorbing particles being selected from a chemical compound comprising an element of an atomic number of at least 37, more preferably of at least 57. Advantageously, the X-ray absorbing particles may be provided in the form of mineral particles for determining the refractive index of said filling member, as described above. Preferably, particles selected from a ytterbium compound are employed for this purpose, in particular ytterbium flouride and/or ytterbium oxide.

In order to achieve the above described properties with respect to an imitation of natural dentine by the filling member, while still ensuring a high flexural strength of the filling member, a fraction of at least 40% in volume of the total content of said filling member is constituted by the fibers. More preferably, the fiber content represents at least 70% of the total volume, and most preferably about 80% of the total volume. This material exceeds currently used materials with respect to its fatigue properties under repeated stress, in particular by at least a factor of five. A further improvement of the flexural strength and the elastic properties of the filling member can be achieved by pretensioning the fibers during the manufacturing process, in particular by a tension force of at least 50 N, more preferably of at least 100 N. Such a tensioning of the fibers can be advantageously implemented during a fabrication process that is carried out by means of pultrusion.

In order to improve the bonding interaction between the fibers and the resin, the circumferential surface of the fibers is preferably covered with a coupling agent, in particular silane, for enhancing the adhesion of said fibers to the resin. On the one hand, such a treatment of the fibers helps to increase the interlaminate shear strength (IS S) of the filling member. In this way, an ISS-value of at least 80 MPa, in particular about 90 MPa or higher, can be achieved, resulting in a further improvement of the fatigue properties under repeated stress. On the other hand, a delamination of the filling member can be effectively avoided, in particular during a reworking of its prefabricated shape, for instance by grinding or cutting the surface of the filling member by means of diamond burs or discs. This advantageously allows adaptation of the shape of the filling member to specific local requirements, even after it is inserted in the jacket member that is anchored in a jawbone.

Preferably, the shape of the filling member is substantially symmetrical with respect to a longitudinal axis of the filling member. In particular a cylindrical, cylindro-conical, conical, spherical or hyperbolic shape or a combination thereof is conceivable. More preferably, the filling member has a substantially hyperbolic form. Most preferably, at least the apical side of the filling member extending into the cavity is shaped as a hyperboloid tapering in the apical direction. Additionally or alternatively, the abutment portion of the filling member or an abutment fixed on the filling member is preferably shaped as a hyperboloid tapering in the coronal direction. Such a hyperboloid may be geometrically described in a x-y-z coordinate system by the general equation $x^2/a^2+y^2/b^2-z^2/c^2=1$, wherein a, b, c are predefined constant values.

More preferably, a circular hyperboloid is used, wherein a substantially equals b in the above equation. Such a hyperbolic form has the advantage of strengthening the overall tooth structure, in particular providing a reduced risk of breakage, combined with a better distribution of lateral forces that are transmitted from the prosthetic structure. Another advantage is provided in conjunction with the reworkability of the filling member, in particular the abutment portion, by means of commonly used cutting tools, such as diamond burs and/or disks, since the hyperbolic form allows an easier adaptation to a specific shape and reduces the tendency of fracture of the abutment during the cutting or grinding procedure.

In order to further improve the bonding interaction of the filling member, mechanical retention structures are preferably applied at the surface of the filling member. According to a first preferred configuration, the mechanical retentions can be provided in a micrometer sized range by trimming the surface of the filling member with appropriate cutting burs or tools.

According to a second preferred configuration, the mechanical retentions can be provided by means of at least one retention groove that is provided at the circumferential surface of the filling member. Preferably, at least two longitudinal grooves are provided extending in the apical direction of the filling member, wherein the course of each groove extends over a different portion of the circumference of the filling member. In this way, an improved retention can be achieved, whereby the danger of a structural weakening of the filling member is minimised. More preferably, the groove extends over the whole length of the filling member in order to increase mechanical retention along its total length. Moreover, the groove preferably exhibits an inclined course with respect to the longitudinal axis of the filling member for allowing an improved retention, in particular a substantially helical form that is at least partially winding or wrapped around the filling member. The preferred width and/or depth of the grooves is at least 0.01 mm and at most 1 mm, a range between 0.1 mm and 0.5 mm being more preferred. Preferably, at most ten, more preferably at most five, retention grooves are provided in order to minimize structural weakening of the filling member and/or the abutment. Other preferred characteristics of such a retention groove are described in patent application No. EP 2 281 525 A2, which is hereby incorporated by reference. According to a third preferred configuration, an improved retention of the dental prosthesis on the filling member is achieved by combining both types of retention structures.

With respect to a separate abutment that is applied on the filling member of the implant, the contact surface of the abutment is preferably constituted by a substantially flat bottom surface at the apical end of the body portion of the abutment. This allows an easy application and positioning of the abutment on the dental implant before its actual fixation. Various fixation methods of the abutment on the implant are conceivable, in particular cementing, screwing or clipping or a combination thereof. Fixation by screwing can be achieved by means of an inward thread or an outward thread in or on the abutment. A particularly advantageous fixation of the abutment on the implant can be achieved in that a receiving bore is provided at the contact surface for receiving a connector portion of the dental implant. Alternatively, a connector portion can be provided at the contact surface configured for insertion into a receiving bore an the dental implant. In particular the cross section of the receiving bore may exhibit a circular, squared, triangular, hexagonal or octogonal shape. In this way, a cost efficient and yet easy applicable and reliable fixation can be realized.

According to a preferred implementation of the filling member, the optical properties of the fiber-reinforced resin structure are exploited for an advantageous light conduction through the filling member, which can be applied to achieve a proper polymerization of a setting product, such as composite resin cement. Advantageously, the ordered arrangement of the fibers extending over the total length of the filling member can be exploited to allow a superior light conduction both through the resin and through the optical fibers. Preferably, the optical fibers are glass fibers, in particular to provide an optical resemblance to natural dentine. Preferably, the apical surface of the filling member is used as a light entering surface. In particular, a planar cutting or grinding of the fibers may be applied for achieving an effective coupling of light into the fibers. Preferably, the light conduction to the apical surface is exploited for cementing the filling member to the jacket member.

Various fabrication methods can be applied for producing the described filling member, in particular extrusion, injection molding, wetting or pultrusion. Preferably, a pultrusion process is applied in which the fibers are pulled through a resin bath containing the above described mineral particles. Before the pultrusion, the fibers are preferably treated with a coupling agent, in particular silane, for enhancing the adhesion of said fibers to the resin. During the pultrusion process, the fibers are preferably tensioned by applying a force of at least 50 N, more preferably at least 100 N, to increase the flexural strength and the elastic properties of the filling member according to the above description. After the pultrusion process, the shaping of the filling member can be achieved by molding and/or turning and/or grinding. Preferably, a turning lathe is used for this purpose.

BRIEF DESCRIPTION OF THE DRAWINGS

The invention will be described in more detail in the following description of preferred exemplary embodiments with reference to the accompanying drawings. In the drawings.

DETAILED DESCRIPTION OF THE PREFERRED EMBODIMENTS

Figure 1:
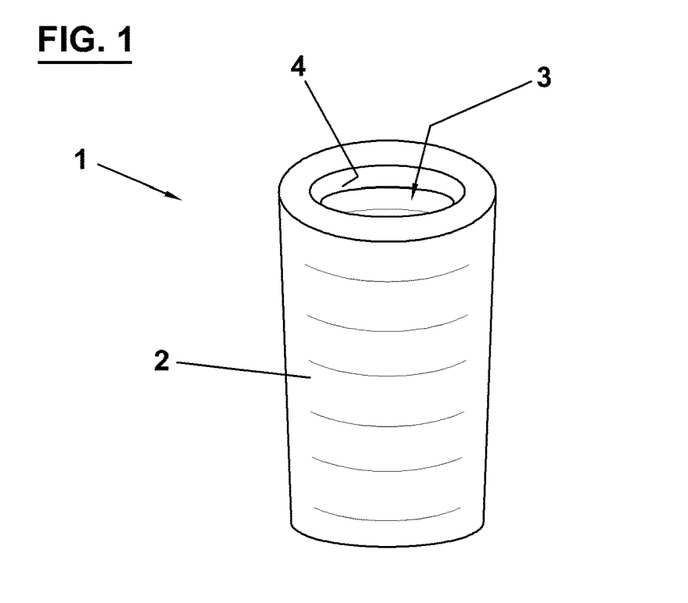
FIGS. 1-5 are schematic perspective views of various constituents of a dental implant.

FIG. 1 depicts an anchoring member 1 constituting a first component of a dental implant. The anchoring member 1 is configured to be anchored into a jawbone and comprises an anchoring wall 2 consisting of titanium, stainless steel, ceramics or another osseointegratable material. The anchoring wall 2 encloses an anchoring cavity 3 extending in an apical direction, wherein the cross section of the cavity 3 continously decreases in the apical direction. The anchoring member 1 comprises a coronal opening 4 in which other constituents of the implant are insertable. The anchoring wall 2 can have an essentially smooth outer surface or it can be provided with retention structures to improve the anchoring in the bone tissue. The thickness of the anchoring wall increases in the apical direction.

Figure 2:
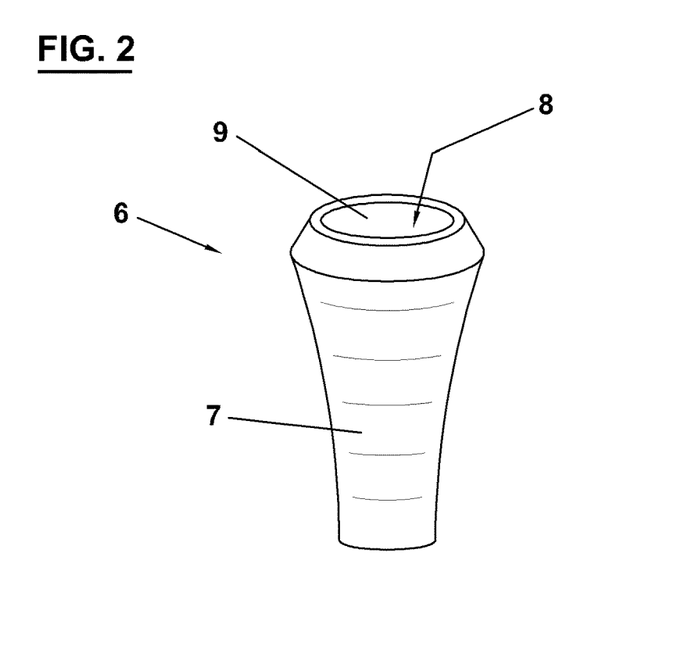

FIG. 2 depicts a sleeve member 6 constituting a second component of the dental implant. The sleeve member 6 is insertable into and removable from the anchoring cavity 3 of anchoring member 1 via its coronal opening 4. For this purpose the sleeve member 6 comprises a sleeve wall 7 with an outer shape substantially corresponding to the shape of the anchoring cavity 3 and consisting of the same material as the anchoring member 1. Once inserted, the sleeve member 6 can be fixed inside the anchoring cavity 3 by means of cementing, screwing, clipping or the like. The sleeve wall 7 encloses a sleeve cavity 8 and comprises a coronal opening 9 in which other constituents of the implant are insertable. The sleeve wall 7 exhibits a substantially constant thickness towards the apical direction.

Figure 3:
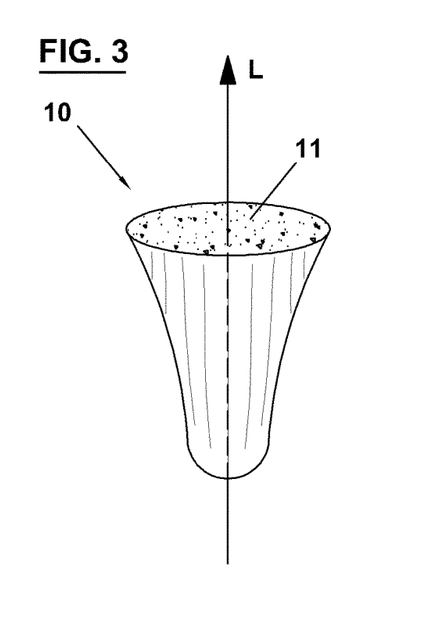

FIG. 3 depicts a filling member 10 constituting a third component of the dental implant. The filling member 10 is insertable into the sleeve cavity 8 of sleeve member 6 via its coronal opening 9. The shape of the filling member 10 is chosen so as to completely fill out the sleeve cavity 8. Furthermore, the shape is symmetrical with respect to a longitudinal axis L and substantially corresponds to a hyperboloid extending in the apical direction. This allows a homogenous lateral transmission of the forces towards the jawbone and also reduces the risk of breakage of the fibrous filling structure. The filling member 10 has a substantially flat coronal surface 11. The length of filling member 10 along axis L substantially corresponds to the length of the sleeve cavity 8. Thus, when inserted into the sleeve cavity 8, the coronal face of the dental implant is essentially planar. Advantageously, the filling member 10 and sleeve member 6 can be provided as two separate pieces or as a single piece, in which the filling member 10 is fixed into the cavity 8 of sleeve member 6 before mounting in a jawbone.

Figure 4:
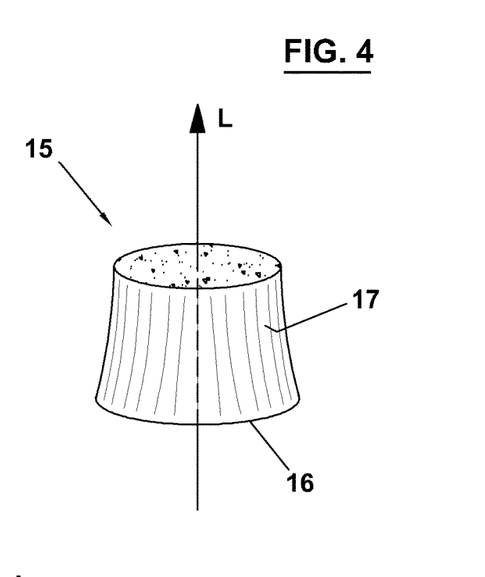

FIG. 4 depicts an abutment 15 that can be attached to the coronal surface 11 of the filling member 10. For this purpose, the abutment 15 has an apical contact surface 16 with a shape substantially corresponding to the shape of the coronal surface 11 of the filling member 10. One or both of the two surfaces can be provided with a connector portion and/or a corresponding receiving bore. At the body portion 17 of the abutment, a dental prosthesis can be attached. The body portion 17 tapers in the coronal direction in order to improve the lateral distribution of forces transmitted from a prosthetic structure.

Figure 5:
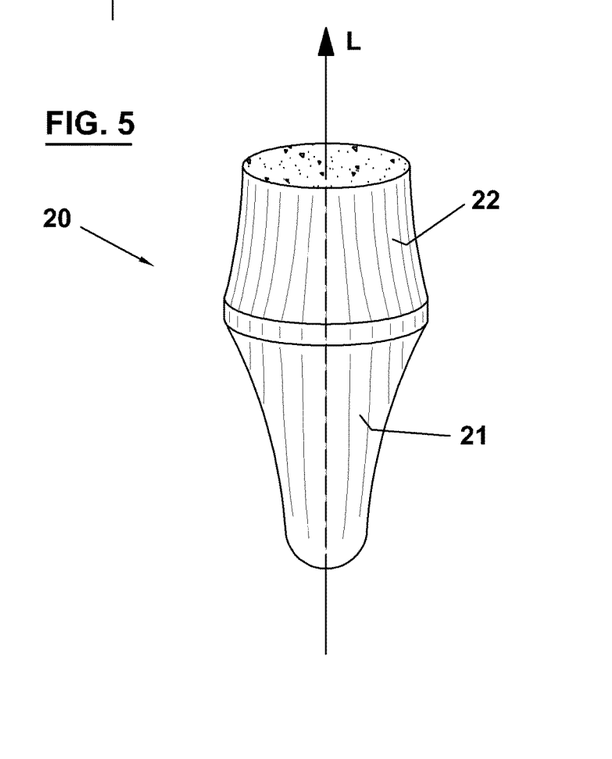

FIG. 5 depicts a filling member 20 consisting of an apical filling portion 21 and a coronal abutment portion 22 made of one piece. The shape and size of filling portion 21 corresponds essentially to the filling member 10 shown in FIG. 3. The shape and size of abutment portion 22 corresponds essentially to the abutment 15 shown in FIG. 4. Thus, when inserted into the sleeve cavity 8, the abutment 22 sticks out from the coronal opening 9 of sleeve member 6.

Figure 14:
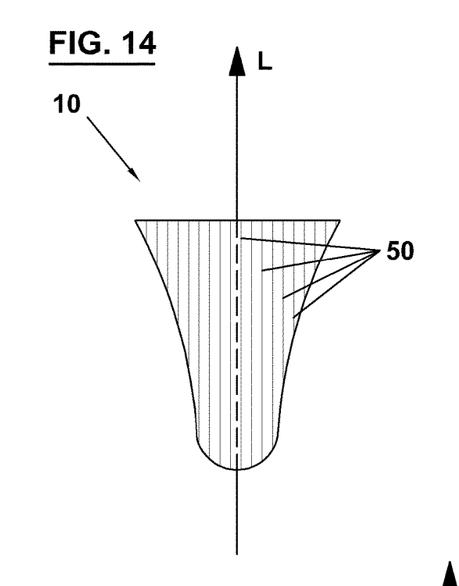
FIGS. 14-16 are schematic sectional views of the constituents of a dental implant shown in FIGS. 3-5.
Figure 15:
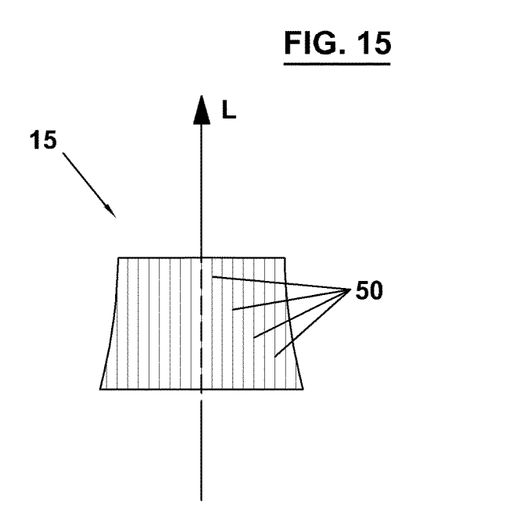
Figure 16:
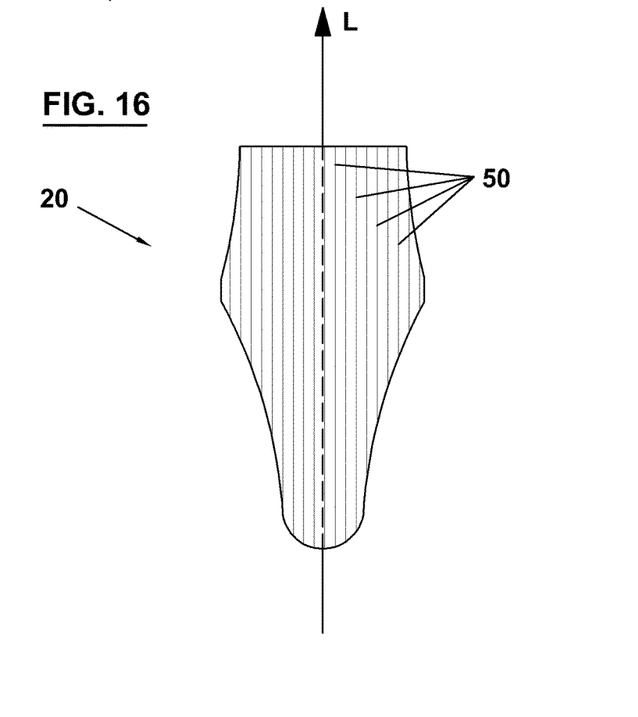

The filling member 10, 20 and the abutment 15 are composed of a resin that is reinforced with fibers 50 extending over the total length of these constituents, as shown in FIGS. 14-16. According to a first embodiment, the fibers are uniformly directed in parallel with respect to the longitudinal axis L. According to a second embodiment, the fibers are arranged in the manner of a braided netting in a biaxial or multiaxial orientation. The resin includes a polymer derived from a methacrylate monomer, preferably methyl methacrylate (MMA) or urethane dimethacrylate (UDMA). Mineral particles, preferably ytterbium flouride and/or ytterbium oxide, are homogenuosly distributed within the resin. The fibers are constituted by glass fibers, wherein the fiber content represents ideally 80% of the volume of the filling member 10, 20 and/or the abutment 15. The fibers are treated with silane as a coupling agent to the resin matrix.

The filling member 10, 20 and the abutment 15 exhibit several advantageous mechanical properties, in particular an elastic modulus similar to natural dentine that is anisotropic with respect to the longitudinal axis L and varying between 13 to 45 GPa. Nevertheless, the filling member 10, 20 and the abutment 15 have a high flexural strength of about 1600 MPa for fracture resistance and durability. Moreover, the interlaminate shear strength (ISS) of the bond between the fibers and the resin matrix is larger than 90 Mpa, leading to an improved value of its fatigue properties under repeated stress when compared to competing materials such as titanium, stainless steel or ceramics. The shape of filling member 10, 20 and abutment 15 can be easily reworked by means of common cutting tools such as diamond burs and/or discs.

Furthermore, the filling member 10, 20 and the abutment 15 have several advantageous optical properties. First, the incorporation of the mineral particles is chosen so that the material composition of glass fibers, resin and mineral particles yields an index of refraction of 1.52. This value corresponds closely to the refractive index of natural dentine (1.540). Secondly, the particular arrangement of the fibers in the resin allows good light conduction, in particular in the apical direction. This can be exploited for a proper polymerization of a setting product, such as resin cement, in particular for fixing the abutment 15 at its contact surface 16 to the coronal surface 11 of the filling member 10 and/or the filling member 10, 20 to the inner surface of the sleeve wall 7 of sleeve member 6.

The mineral particles with a high atomic number embedded in the resin lead to a radiopacity of the filling member 10, 20 and the abutment 15 that is larger than 200% of the value of the radiopacity of Aluminium, more preferably above a value of 400% of the radiopacity of Aluminium. The chemical composition of the resin material similar to composite resin cement permits a chemically profound bonding-interaction between the abutment 15 and the filling member 10 and between the filling member 10, 20 and the inner surface of the sleeve wall 7 of sleeve member 6.

Figures 6, 7, 8, 9, 10:
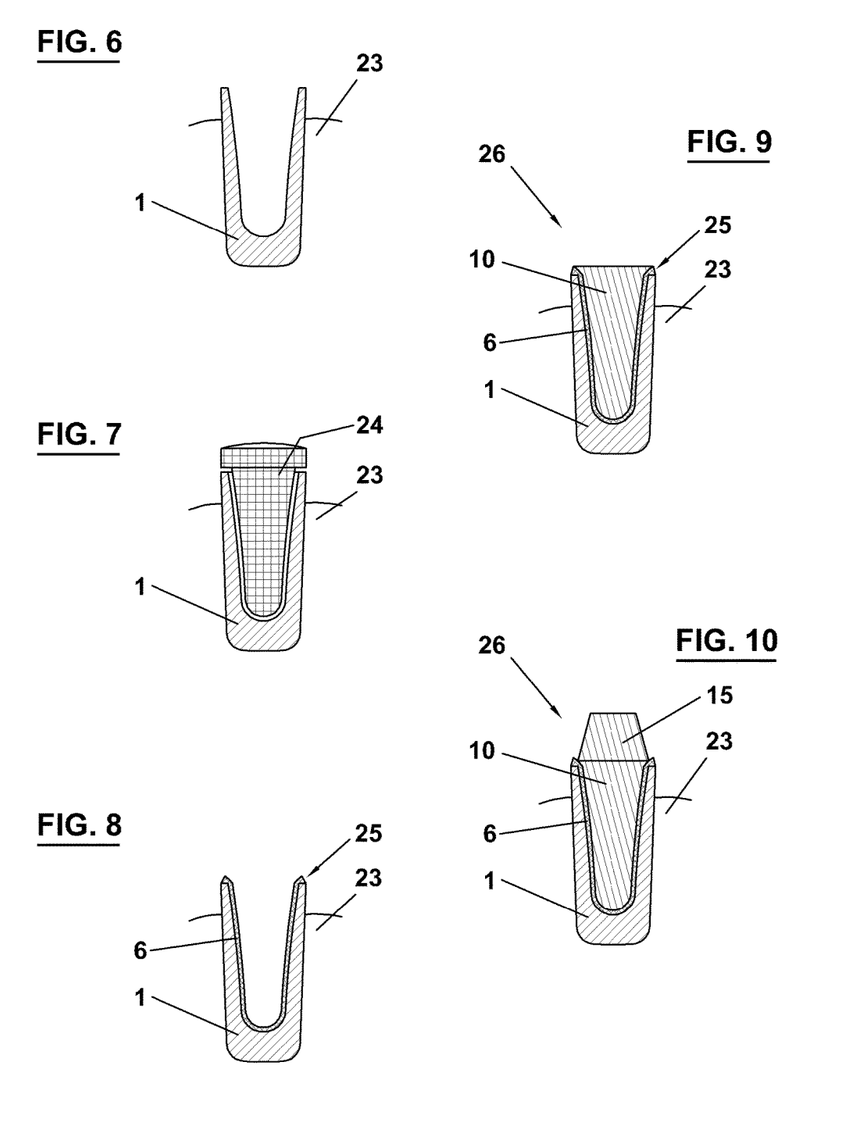
FIGS. 6-10 are schematic sectional views illustrating a method for mounting an artificial tooth structure comprising the constituents of a dental implant shown in FIGS. 1-5.

In FIGS. 6-10 a method for mounting the dental implant is illustrated. In a first step, as shown in FIG. 6, the anchoring member 1 is implanted into the jawbone 23. After the surgical intervention, a healing cap 24 is temporarily inserted into the anchoring cavity 3, as depicted in FIG. 7.

After the healing, the healing cap 24 is replaced by the sleeve member 6, as shown in FIG. 8. The sleeve member 6 is fixed by cementing, clipping or screwing. The combined system composed of anchoring member 1 and sleeve member 6 constitutes a jacket member 25 which serves as a secure container for receiving filling member 10, 20. According to an alternative embodiment, the jacket member 25 consists of one piece, that can be anchored into the jawbone. For instance, the jacket member 25 may be constituted only by anchoring member 1.

In the next step illustrated in FIG. 9, the filling member 10 is inserted into the sleeve cavity 8. The filling member 10 is fixed by cementing, clipping or screwing. The combined system composed of jacket member 25 and filling member 10 constitutes a dental implant 26. Finally, as shown in FIG. 10, the abutment 15 can be fixed on the coronal side of the dental implant 26 and serve as a support for a dental prosthesis. Alternatively, the filling member 20 with an abutment portion 22 can be inserted into the sleeve cavity 8 in order to provide the abutment 22 without an extra step.

According to an alternative embodiment of the described method, the sleeve member 6 and the filling member 10, 20 are provided in one piece that is inserted into the cavity 3 of anchoring member 1 in a single step.

Figure 11:
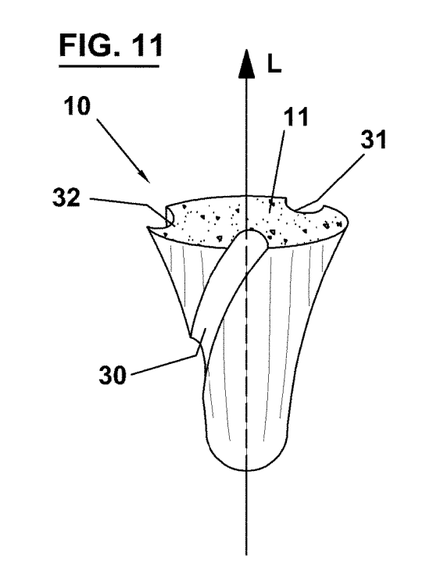
FIGS. 11-13 are schematic perspective views of alternative embodiments of the constituents of a dental implant shown in FIGS. 3-5.

In FIG. 11 an alternative embodiment of filling member 10 is depicted. Three retention grooves 30, 31, 32 are provided at the lateral surface of the hyperbolic surface. Each of the retention grooves 30, 31, 32 extends over a different circumferential portion of this surface in order to avoid a weakening of the structure and a risk of breakage. The course of retention grooves 30, 31, 32 substantially extends in the apical direction and over part of the circumference of the filling member 10 such that they are partially wrapped around the hyperbolic surface. In this way, the retention properties can be greatly improved when the filling member 10 is fixed in the cavity 8 by means of resin cement. Preferably, the grooves 30, 31, 32 extend over the total length of the filling member 10 to increase mechanical retention along the total device length.

Figure 12:
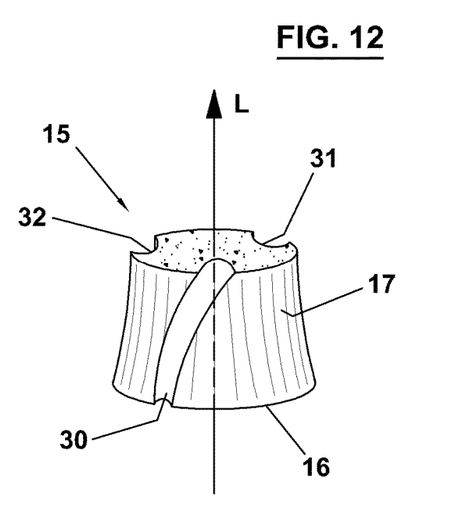
Figure 13:
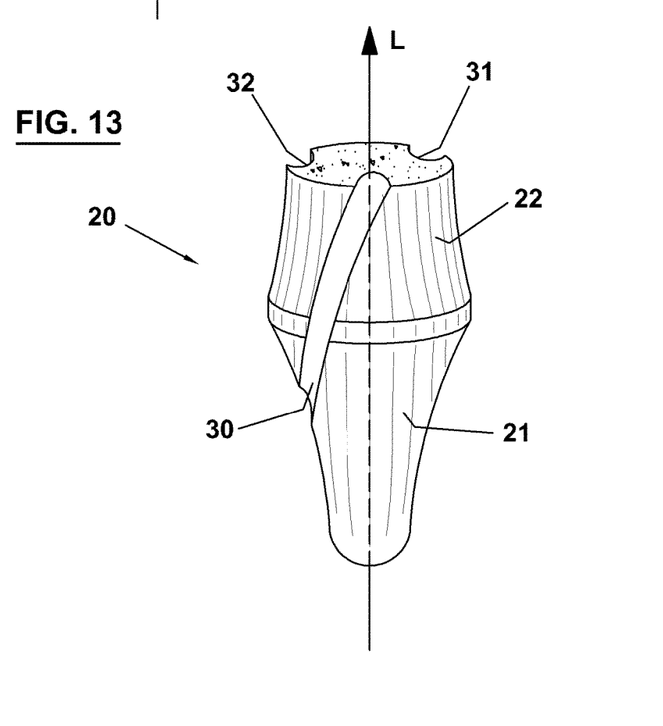

FIG. 12 shows an embodiment of the abutment 15 in which the body portion 17 of the abutment 15 is provided with corresponding retention grooves 30, 31, 32. FIG. 13 shows an embodiment of filling member 20 comprising corresponding retention grooves 30, 31, 32 each extending over the total length of the filling portion 21 and the abutment portion 22 and over a different circumferential surface portion of filling member 20 in order to avoid structural weakening.

The above described preferred embodiments are intended to illustrate the principles of the invention, but not to limit the scope of the invention. Various other embodiments and modifications to those preferred embodiments may be made by those skilled in the art without departing from the scope of the present invention.

The invention claimed is:
1. A dental implant configured to be implanted in a jawbone for supporting a dental prosthesis, the dental prosthesis replacing a natural tooth, the dental implant comprising:
   a jacket member including at least in part an osseointegratable material and enclosing a cavity in an apical direction, a thickness of a wail of the jacket member enclosing the cavity continuously increasing along the apical direction such that a size of a cross-section of the cavity continuously decreases along the apical direction, the jacket member being more stiff and brittle than dentine and cementum of a natural tooth, and
   a filling member consisting of fiber reinforced material and being shaped so as to substantially fill said cavity, wherein:
   said filling member is composed of a resin that is reinforced with fibers, the fibers extending over the total length of said filling member,
   said fibers are glass fibers,
   said resin is derived from at least one methacrylate monomer,
   mineral particles are embedded in said resin, said mineral particles comprising X-ray absorbing particles of a ytterbium compound,
   a fraction of at least 40% in volume of the total content of said filling member is constituted by said fibers of said fiber reinforced material, said filling member exhibits a modulus of elasticity of at least 10 GPa and at most 50 GPa,
at least an apical side of said filling member extending into said cavity is shaped as an hyperboloid tapering in the apical direction, said shape of said hyperboloid being geometrically described in an x-y-z coordinate system by the general equation $x^2/a^2+y^2/b^2-z^2/c^2=1$, with a, b, and c being predefined constant values,
said modulus of elasticity is lower for a force applied perpendicularly to a longitudinal axis of said filling member than for a force applied parallel to said longitudinal axis, and
said filling member mimics at least the modulus of elasticity and optical properties of natural dentine.

2. The dental implant according to claim 1, wherein said cavity constitutes at least one third of the volume of said jacket member.

3. A dental implant configured to be anchored in a jawbone for supporting a dental prosthesis, the dental implant comprising:
a jacket member including at least in part an osseo-integratable material and enclosing a cavity in an apical direction, the jacket member being more stiff and brittle than dentine and cementum of a natural tooth, and
a filling member including fiber reinforced material and being shaped so as to substantially fill said cavity,
wherein:
said filling member is composed of a resin that is reinforced with fibers, the fibers extending over the total length of said filling member,
said fibers are glass fibers,
said resin is derived from at least one methacrylate monomer,
a fraction of at least 40% in volume of the total content of said filling member is constituted by the fibers of said fiber reinforced material,
said jacket member comprises an anchoring member including the osseo-integratable material and a rigid sleeve member that is insertable into said anchoring member during mounting of said dental implant and is removable from said anchoring member, such that said cavity is enclosed by said sleeve member,
said jacket member comprises a coronal opening and said filling member is insertable into said jacket member during mounting of said dental implant, said filling member being insertable into said sleeve member through said coronal opening,
a thickness of a wall of said anchoring member continuously increases along the apical direction and a thickness of a wall of said sleeve member enclosing said cavity is constant along the apical direction such that a size of a cross-section of said cavity continuously decreases along the apical direction,
said filling member exhibits a modulus of elasticity of at least 10 GPa and at most 50 GPa,
at least an apical side of said filling member extending into said cavity is shaped as an hyperboloid tapering in the apical direction, said shape of said hyperboloid being geometrically described in an x-y-z coordinate system by the general equation $x^2/a^2+y^2/b^2-z^2/c^2=1$, with a, b, and c being predefined constant values,
said modulus of elasticity is lower for a force applied perpendicularly to a longitudinal axis of said filling member than for a force applied parallel to said longitudinal axis, and
said filling member mimics at least the modulus of elasticity of natural dentine.

4. The dental implant according to claim 3, wherein said coronal opening extends over at least 50% of a coronal end of said jacket member.

5. The dental implant according to claim 1, wherein said jacket member comprises walls with an increasing thickness towards an apical end of the jacket member.

6. The dental implant according to claim 1, wherein said jacket member comprises walls with a thickness of at most 10 mm for enclosing said cavity.

7. The dental implant according to claim 1, wherein a coronal height of said filling member substantially corresponds to a coronal height of said cavity.

8. The dental implant according to claim 1, wherein a coronal height of said filling member exceeds a coronal height of said cavity, wherein the exceeding portion terminating at a coronal end of said filling member constitutes an abutment for a dental prosthesis.

9. The dental implant according to claim 1, wherein at least part of said fibers are substantially uniformly directed-in parallel with respect to a longitudinal axis of said filling member.

10. The dental implant according to claim 1, wherein at least part of said fibers are arranged in the manner of a braided netting in a biaxial or multiaxial orientation.

11. The dental implant according to claim 1, wherein the at least one methacrylate monomer is at least one of methyl methacrylate (MMA) and urethane dimethacrylate (UDMA).

12. The dental implant according to claim 1, wherein X-ray absorbing particles are embedded in said resin, said X-ray absorbing particles being selected from a chemical compound comprising an element with an atomic number of at least 37.

13. The dental implant according to claim 1, wherein at least one retention groove is provided at a circumferential surface of said filling member.

14. The dental implant according to claim 1, wherein the cavity constitutes at least one half of the volume of said jacket member.

15. The dental implant according to claim 3, wherein said coronal opening extends over at least 70% of a coronal end of said jacket member.

16. The dental implant according to claim 1, wherein said jacket member comprises walls with a thickness of at most 3 mm for enclosing said cavity.

17. The dental implant according to claim 1, wherein a fraction of at least 70% in volume of the total content of said filling member is constituted by the fibers of said fiber reinforced material.

18. A dental implant configured to be anchored in a jawbone for supporting a dental prosthesis, the dental implant comprising:
a jacket member including at least in part an osseo-integratable material and enclosing a cavity in an apical direction, the jacket member being more stiff and brittle than dentine and cementum of a natural tooth, and
a filling member including fiber reinforced material and being shaped so as to substantially fill said cavity,
wherein:
said filling member is composed of a resin that is reinforced with fibers, the fibers extending over the total length of said filling member,
said resin is derived from at least one methacrylate monomer,
said jacket member comprises an anchoring member including the osseo-integratable material and a rigid sleeve member that is insertable into said anchoring member and is removable from said anchoring member, such that said cavity is enclosed by said sleeve member, said jacket member comprises a coronal opening and said filling member is insertable into said jacket member through said coronal opening after anchoring of the jacket member in a jawbone, and is removable from said jacket member, after mounting of said dental implant, by means of drilling of said filling member, through said coronal opening, said fiber reinforced material of said filling member being chosen such that it permits removal of said filling member by said drilling through said coronal opening by means of a reamer, a thickness of a wall of said anchoring member continuously increases along the apical direction and a thickness of a wall of said sleeve member enclosing said cavity is constant along the apical direction such that a size of a cross-section of said cavity continuously decreases along the apical direction, said filling member exhibits a modulus of elasticity of at least 10 GPa and at most 50 GPa, at least an apical side of said filling member extending into said cavity is shaped as an hyperboloid tapering in the apical direction, said shape of said hyperboloid being geometrically described in an x-y-z coordinate system by the general equation $x^2/a^2 + y^2/b^2 - z^2/c^2 = 1$, with a, b, and c being predefined constant values, said modulus of elasticity is lower for a force applied perpendicularly to a longitudinal axis of said filling member than for a force applied parallel to said longitudinal axis, and said filling member mimics at least the modulus of elasticity of natural dentine.

19. The dental implant according to claim 1, wherein the index of refraction of the filling member is between 1.3 and 1.8.

20. The dental implant according to claim 1, wherein the index of refraction of the filling member is between 1.4 and 1.6.

21. The dental implant according to claim 1, wherein the index of refraction of the filling member is between 1.50 and 1.55.

22. The dental implant according to claim 1, wherein the index of refraction of the filling member is such that the filling member simulates the optical properties of natural dentine.

23. The dental implant according to claim 3, wherein said sleeve member comprises an outer surface corresponding to an inner surface of said anchoring member, said outer surface of said sleeve member fully covering said inner surface of said anchoring member.

24. The dental implant according to claim 18, wherein said sleeve member comprises an outer surface corresponding to an inner surface of said anchoring member, said outer surface of said sleeve member fully covering said inner surface of said anchoring member.

25. The dental implant according to claim 1, wherein said jacket member comprises a coronal opening and said filling member is insertable into said jacket member through said coronal opening, and is removable from said jacket member, after mounting of said dental implant, by means of drilling of said filling member, through said coronal opening.

26. A dental implant configured to be implanted in a jawbone for supporting a dental prosthesis, the dental prosthesis replacing a natural tooth, the dental implant comprising:

a jacket member including at least in part an osseointegratable material and enclosing a cavity in an apical direction, a thickness of a wall of the jacket member enclosing the cavity continuously increasing along the apical direction such that a size of a cross-section of the cavity continuously decreases along the apical direction, the jacket member being more stiff and brittle than dentine and cementum of a natural tooth, and a filling member consisting of fiber reinforced material and being shaped so as to substantially fill out said cavity, wherein:

said filling member is composed of a resin that is reinforced with fibers, the fibers extending over the total length of said filling member, said fibers are glass fibers, said resin is derived from at least one methacrylate monomer, mineral particles are embedded in said resin, said mineral particles comprising X-ray absorbing particles selected from an ytterbium compound, a fraction of at least 40% in volume of the total content of said filling member is constituted by said fibers of said fiber reinforced material, said filling member exhibits a modulus of elasticity of at least 10 GPa and at most 50 GPa, said jacket member comprises a coronal opening and said filling member is insertable into said jacket member through said coronal opening after anchoring of the jacket member in a jawbone, and is removable from said jacket member, after mounting of said dental implant, by means of drilling of said filling member, through said coronal opening, said fiber reinforced material of said filling member is chosen such that it permits removal of said filling member by said drilling through said coronal opening by means of a reamer, said modulus of elasticity is lower for a force applied perpendicularly to a longitudinal axis of said filling member than for a force applied parallel to said longitudinal axis, and said filling member mimics at least the modulus of elasticity and optical properties of natural dentine.

27. The dental implant according to claim 3, wherein the cavity constitutes at least one half of the volume of said jacket member.

28. The dental implant according to claim 18, wherein the cavity constitutes at least one half of the volume of said jacket member.

29. The dental implant according to claim 18, wherein said coronal opening extends over at least 70% of a coronal end of said jacket member.

30. The dental implant according to claim 26, wherein the cavity constitutes at least one half of the volume of said jacket member.

31. The dental implant according to claim 26, wherein said coronal opening extends over at least 70% of a coronal end of said jacket member.

32. The dental implant according to claim 1, wherein a variation of said modulus of elasticity is at least 30 GPa and at most 40 GPa.

33. The dental implant according to claim 1, wherein said modulus of elasticity varies between at most 20 GPa for said force applied perpendicularly to said longitudinal axis of said filling member and at least 30 GPa for said force applied parallel to said longitudinal axis.

34. The dental implant according to claim 3, wherein a variation of said modulus of elasticity is at least 30 GPa and at most 40 GPa.

35. The dental implant according to claim 3, wherein said modulus of elasticity varies between at most 20 GPa for said force applied perpendicularly to said longitudinal axis of said filling member and at least 30 GPa for said force applied parallel to said longitudinal axis.

36. The dental implant according to claim 18, wherein a variation of said modulus of elasticity is at least 30 GPa and at most 40 GPa.

37. The dental implant according to claim 18, wherein said modulus of elasticity varies between at most 20 GPa for said force applied perpendicularly to said longitudinal axis of said filling member and at least 30 GPa for said force applied parallel to said longitudinal axis.

38. The dental implant according to claim 26, wherein a variation of said modulus of elasticity is at least 30 GPa and at most 40 GPa.

39. The dental implant according to claim 26, wherein said modulus of elasticity varies between at most 20 GPa for said force applied perpendicularly to said longitudinal axis of said filling member and at least 30 GPa for said force applied parallel to said longitudinal axis.

* * * * *

UNITED STATES PATENT AND TRADEMARK OFFICE
CERTIFICATE OF CORRECTION

PATENT NO. : 10,342,644 B2
APPLICATION NO. : 13/358785
DATED : July 9, 2019
INVENTOR(S) : Peter Nordin and Harald Nordin It is certified that error appears in the above-identified patent and that said Letters Patent is hereby corrected as shown below:

In the Claims

Claim 1 at Column 10, Line 47, please delete the word "wail" and insert the word --wall--.

Signed and Sealed this
Fourteenth Day of January, 2020

Andrei Iancu
*Director of the United States Patent and Trademark Office*